United States Patent
Liu et al.

(10) Patent No.: US 8,278,445 B2
(45) Date of Patent: Oct. 2, 2012

(54) PREPARATION METHODS OF AZOXYSTROBIN AND ITS ANALOGS

(75) Inventors: Shangzhong Liu, Beijing (CN); Canxian Mu, Beijing (CN); Wenjun Wang, Beijing (CN); Jianwei Chen, Beijing (CN); Shuguang Wang, Beijing (CN)

(73) Assignee: Nutrichem Company Limited, Beijing (CN)

( * ) Notice: Subject to any disclaimer, the term of this patent is extended or adjusted under 35 U.S.C. 154(b) by 291 days.

(21) Appl. No.: 12/668,219

(22) PCT Filed: Sep. 19, 2008

(86) PCT No.: PCT/CN2008/072429
§ 371 (c)(1),
(2), (4) Date: Jan. 8, 2010

(87) PCT Pub. No.: WO2009/052719
PCT Pub. Date: Apr. 30, 2009

(65) Prior Publication Data
US 2010/0179320 A1    Jul. 15, 2010

(30) Foreign Application Priority Data
Oct. 24, 2007  (CN) .......................... 2007 1 0163386

(51) Int. Cl.
*C07D 239/22* (2006.01)
*C07C 69/76* (2006.01)
(52) U.S. Cl. ......................................... 544/319; 560/60
(58) Field of Classification Search .................. 544/319; 560/60; 504/255
See application file for complete search history.

(56) References Cited

U.S. PATENT DOCUMENTS

| | | |
|---|---|---|
| 5,057,146 A | 10/1991 | Anthony et al. |
| 6,162,945 A | 12/2000 | Keil et al. |
| 7,084,272 B2 | 8/2006 | Jackson et al. |
| 2004/0242607 A1 | 12/2004 | Jackson et al. |
| 2006/0229450 A1 | 10/2006 | Jackson et al. |
| 2006/0287527 A1 | 12/2006 | Miyazawa et al. |

FOREIGN PATENT DOCUMENTS

| | | |
|---|---|---|
| CN | 1016611 | 2/1988 |
| CN | 1206401 | 1/1999 |
| CN | 1511144 | 7/2004 |
| CN | 101157657 | 4/2008 |

*Primary Examiner* — James O Wilson
*Assistant Examiner* — Ebenezer O Sackey
(74) *Attorney, Agent, or Firm* — Orrick, Herrington & Sutcliffe, LLP

(57) ABSTRACT

Preparation method of a compound of general formula (I) comprises the following steps: (1) a compound of general formula (II) reacts with a formylating agent in an aprotic solvent at a temperature between −20° C. and 200° C. in the presence of a Lewis acid, then an organic base is added to promote the reaction to obtain an intermediate product; (2) the above intermediate product reacts with a methylating agent in the presence of an alkali at a temperature between −20° C. and 100° C. to obtain the compound of formula (I).

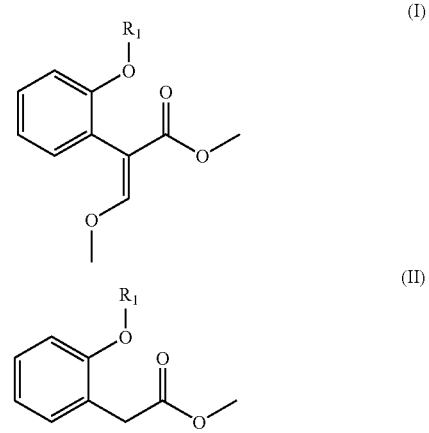

15 Claims, No Drawings

PREPARATION METHODS OF AZOXYSTROBIN AND ITS ANALOGS

TECHNICAL FIELD

The present invention relates to a novel preparation method of azoxystrobin which is an agricultural fungicide and its analogs.

BACKGROUND ART

Azoxystrobin, chemically named methyl (E)-2-(2-(6-(2-cyanophenoxy)pyrimidine-4-oxy)phenyl)-3-methoxyacrylate, is the first commercialized β-methoxyacrylate-based fungicide that was developed by Zeneca Inc. It exhibits a fungi suppressing activity by acting as a mitochondria respiration inhibitor, i.e. inhibiting the respiration of mitochondria by impeding electron transfer between cytochromes b and $C_1$. Azoxystrobin is a highly effective and broad-spectrum fungicide with activity against almost all pathogenic fungi including Oomycetes, Phycomycete, Ascomycota and Deuteromycetes. And it can be used on crops like grain, rice, grape, potato, vegetable, fruit trees, beans and so on by stem or foliar application, or seed treatment. For the above reason, there are many patent documents reporting its synthesis methods, e.g. EP-A-0382375A, WO92/08703A1 and GB229174, etc.

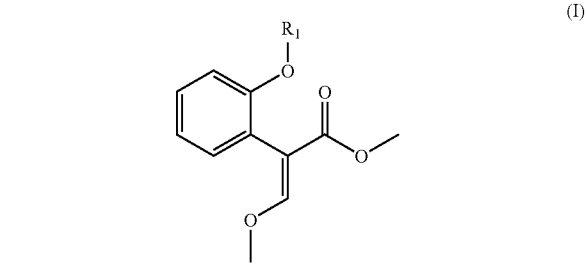

azoxystrobin

The preparation methods which have been reported as yet can be classified into two categories:

(A) O-hydroxyphenylacetic acid, as the starting raw material, is dehydrated to obtain benzofuranone followed by introduction of a methoxymethylene group to benzofuranone's side chain with the use of trimethyl orthoformate or methyl formate. Then the resulting intermediate is condensed with 4,6-dichloropyrimidine and with o-cyanophenol to obtain azoxystrobin. The key point of this method lies in the methoxymethylenation of α-methyl in the benzofuranone and its stability in subsequent reactions. The document first reporting this method is Australian Journal of Chemical, 26(5), 1079-91, 1973 and Journal of Organic Chemistry, 40(24), 3474-80, 1975.

(B) O-hydroxyphenylacetaldehyde is used as the starting material, and the protection of phenolic hydroxy first by benzyl group and a series of reactions are conducted to obtain methyl 2-benzyloxyphenylacetate. Then methoxymethylenation reaction is carried out by reacting methyl 2-benzyloxyphenylacetate with methyl formate in the presence of sodium methoxide. The resulting product is condensed with 4,6-dichloropyrimidine and then with o-cyanophenol to obtain azoxystrobin.

Method (B) is the first introduced synthesis route as well as the first reported synthesis method by patent documents. Despite the synthesis of the product being achieved, it involves additional processes including protection of starting material, de-protection of intermediate product, and a series of conversions.

DISCLOSURE OF THE INVENTION

The present invention aims to provide a novel method for preparing a compound of general formula (I), which has a simplified production process and increased productivity:

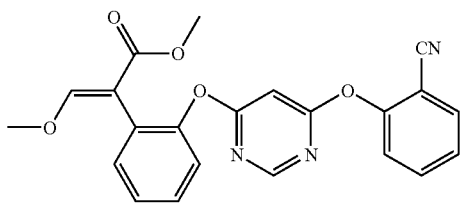

(I)

wherein $R_1$ is a hydrogen atom, a $C_1$-$C_{10}$ hydrocarbon group, 6-(2-cyanophenoxypyrimidin)-4-yl or pyrimidin-4-yl substituted by a halogen atom at site 6.

In the specification, the term "halogen" includes fluorine, chlorine, bromine and iodine, preferably chlorine and bromine.

The method for preparing a compound of general formula (I) according to the present invention comprises the steps of:

(1) conducting a formylation reaction by reacting a compound of general formula (II) with a formylating agent in an aprotic solvent in the presence of a Lewis acid at a temperature ranging from −20° C. to 200° C., and adding an organic base to promote the reaction so that an intermediate product is obtained,

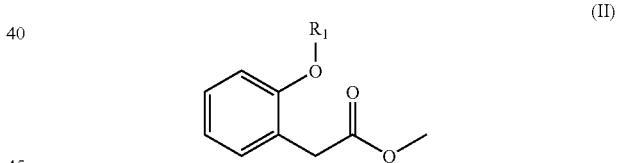

(II)

wherein $R_1$ has the same definition as $R_1$ in general formula (I);

(2) conducting a methylation reaction by reacting the intermediate product obtained in step (1) with a methylating agent in the presence of an alkali at a temperature ranging from −20° C. to 100° C. to obtain the compound of general formula (I).

Without any limitation or exclusion, the Lewis acid used in the present invention generally refers to all Lewis acid known to one skilled in the art, such as titanium tetrachloride, aluminum trichloride, methylaluminum chloride, tin chloride, ferric chloride, zinc chloride and boron trifluoride ethyl ether, preferably titanium tetrachloride. The amount of the Lewis acid used should ensure the smoothness of the formylation reaction, for example, 0.1 to 6.0 molar equivalent, preferably 1.0 to 3.0 molar equivalent, per 1.00 molar equivalent of the compound of general formula (II) used.

The formylating agent used in the present invention includes all formylating agents known to one skilled in the art, such as methyl formate, ethyl formate, trimethyl orthoformate and triethyl orthoformate, preferably trimethyl orthoformate. The amount of the formylating agent used should ensure the smoothness of the formylation reaction, for example, 1.0 to 10.0 molar equivalent, preferably 1.0 to 3.0 molar equivalent, per 1.00 molar equivalent of the compound of general formula (II) used.

The organic base used in the present invention include all kinds of organic bases, such as amine and metal alkoxide, preferably tertiary amine like trimethyl amine, triethyl amine, tributyl amine, diisopropylethyl amine, pyridine and so on. The amount of the organic base used should ensure the smoothness of the reaction, for example, 0.2 to 10.0 molar equivalent, preferably 2.0 to 6.0 molar equivalent, per 1.00 molar equivalent of the compound of general formula (II) used.

The alkali used in the present invention includes all inorganic and organic bases known to one skilled in the art, such as sodium hydroxide, potassium hydroxide, sodium carbonate, potassium carbonate, sodium bicarbonate, potassium bicarbonate, sodium methoxide, sodium ethoxide and sodium tertiary butoxide, preferably sodium hydroxide and potassium hydroxide. The amount of the alkali used should ensure the smoothness of the methylation reaction, for example, 0.8 to 6.0 molar equivalent, preferably 1.0 to 2.0 molar equivalent, per 1.00 molar equivalent of the compound of general formula (II) used.

The methylating agent used in the present invention includes all methylating agents, such as dimethyl sulfate, trimethyl orthoformate, chloromethane, bromomethane and iodometharie, preferably dimethyl sulfate. The amount of the methylating agent used should ensure the smoothness of the methylation reaction, for example, 0.8 to 6.0 molar equivalent, preferably 1.0 to 3.0 molar equivalent, per 1.00 molar equivalent of the compound of general formula (II) used.

It is preferable to conduct the formylation reaction in an aprotic solvent, which is unable to donate or accept protons. The example of aprotic solvent includes halogenated hydrocarbon, benzene, saturated hydrocarbon, dimethyl sulfoxide, etc., preferably halogenated hydrocarbon such as dichloroethane, dichloromethane, trichloromethane and chlorobenzene.

The medium suitable for conducting the methylation reaction may be a polar or a non-polar solvent, such as benzene, toluene, chlorobenzene, dichloromethane, dichloroethane, methanol, ethanol, butanol, ethyl ether, 1,2-dimethoxyethane, tetrahydrofuran, acetone, methyl ethyl ketone, methyl isobutyl ketone, ethyl acetate, isopropyl acetate, propyl acetate and butyl acetate, etc.

In the method according to the present invention, a compound of general formula (II) reacts with a formylating agent in an aprotic solvent in the presence of a Lewis acid at a temperature ranging from −20° C. to 200° C., preferably from −20° C. to 100° C., more preferably from −10° C. to 50° C., and particularly preferably from −5° C. to 5° C., under stirring. After a period of time, an organic base is added to promote the reaction under further stirring. Then an organic acid such as formic acid, acetic acid and so on, or an inorganic acid such as hydrochloric acid, phosphoric acid, sulfuric acid and so on, is added to quench the reaction. The obtained intermediate product is separated from the mixture, and then reacts with a methylating agent in a medium of methylation reaction in the presence of an alkali at a temperature ranging from −20° C. to 100° C., preferably from −10° C. to 80° C., more preferably from 10° C. to 60° C. After the reaction is completed, a compound of general formula (I) which is the resulting product is separated from the mixture.

The synthesis scheme of the fungicide of azoxystrobin according to the present invention is advantageous in that the starting raw material is cheap and easily accessible, and the process is environmentally friendly, conducted under a mild condition and has a high yield.

BEST MODE FOR CARRYING OUT THE INVENTION

The following examples are presented for the purpose of elaborating on the present invention, and the content and scope of protection claimed by the present application are not limited by them.

EXAMPLE 1

Preparation of methyl 2-(2-(6-(2-cyanophenoxy) pyrimidine-4-oxy)phenyl)acetate (i.e. the Compound of General Formula (II) When $R_1$ is 6-(2-cyanophenoxypyrimidin)-4-yl)

Under the dried nitrogen atmosphere, to a reaction flask were added 540 mL of dried N,N-dimethylformamide, 26.2 g of 2-hydroxybenzonitrile, 29.8 g of 4,6-dichloropyrimidine and 27.6 g of anhydrous potassium carbonate, and this mixture is heated under stirring to 100. degree. C. to be followed by reacting for 3 hrs. Then, 34.9 g of methyl 2-hydroxyphenylacetate and 13.8 g of anhydrous potassium carbonate were added and the temperature was increased to 120. degree. C. The reaction went on under stirring for 5 hrs. Afterwards, N,N-dimethylformamide was recovered by concentrating the reaction mixture under reduced pressure, 150 mL of toluene and 100 mL of water were added to the residue to dissolve the solid under stirring. The solution was left to stand still for separation of an organic phase and an aqueous phase. The organic phase was concentrated to obtain .a solid crude product of methyl 2-(2-(6-(2-cyanophenoxy)pyrimidine-4-oxy) phenyl)acetate. After purification, 54 g of amber solid was obtained from the crude product with a yield of 75%.

Melting point: 95-96° C.;

$^1$H NMR (500 NMR, CDCl$_3$): δ 3.61 (s, 3H), 3.62 (s, 2H), 6.54 (d, 1H), 7.16 (q, 1H), 7.28 (m, 1H), 7.33 (m, 1H), 7.32-7.41 (m, 3H), 7.67 (m, 1H), 7.23 (q, 1H), 8.39 (d, 1H).

EXAMPLE 2

Preparation of methyl (E)-2-(2-(6-(2-cyanophenoxy)pyrimidine-4-oxy) phenyl)-3-methoxyacrylate (i.e. azoxystrobin)

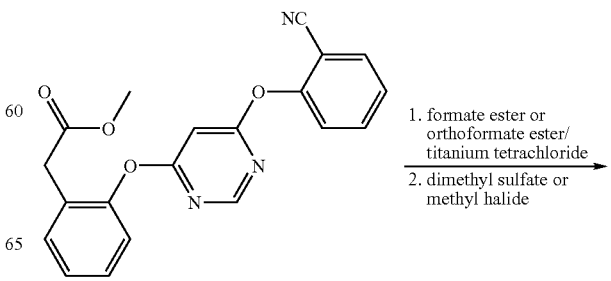

1. formate ester or orthoformate ester/ titanium tetrachloride
2. dimethyl sulfate or methyl halide

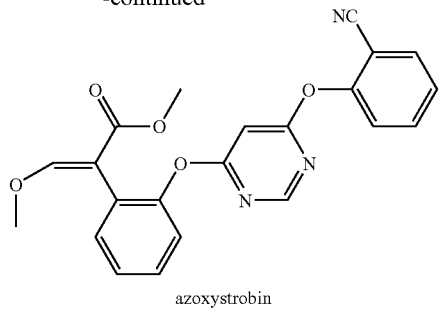

azoxystrobin

Under the dried nitrogen atmosphere, to a reaction flask were added 150 mL of dichloromethane and 11.4 g of titanium tetrachloride, and then 6.4 g of trimethyl orthoformate was further added under violent stirring. After being stirred at room temperature for 1 hr, the mixture was cooled to −5° C., followed by adding thereto 18.1 g of methyl 2-(2-(6-(2-cyanophenoxy)pyrimidine-4-oxy)phenyl)acetate. The resultant was stirred for 30 min, and then 12.1 g of triethylamine was added and the resultant was stirred for 1 hr. The resulting reaction mixture was washed with 40 mL of 10% hydrochloric acid, dried with anhydrous magnesium sulfate and evaporated under vacuum to obtain a brown viscous substance. After the brown viscous substance was dissolved in 100 mL of hot toluene, the solution was cooled to room temperature. Then 0.9 g of benzyltriethylammonium chloride, 15 g of 20% sodium hydroxide aqueous solution and 12.6 g of dimethyl sulfate were added. The mixture was stirred at room temperature for 5 hrs, and then heated to 50° C. and maintained for another 1 hr under stirring. The resulting mixture was washed with 50 mL of water, evaporated under reduced pressure and purified with flash column chromatography to obtain 18.5 g yellow solid. The yield was 92%.

Melting point: 115-116° C.;
$^1$H NMR (500 NMR, CDCl$_3$): δ 3.64 (s, 3H), 3.75 (s, 3H), 6.42 (d, 1H), 7.22 (q, 1H), 7.29-7.43 (m, 5H), 7.49 (s, 1H), 7.66 (m, 1H), 7.10 (q, 1H), 8.40 (d, 1H).

EXAMPLE 3

Preparation of methyl (E)-2-(2-(6-chloropyrimidine-4-oxy)phenyl)-3-methoxyacrylate

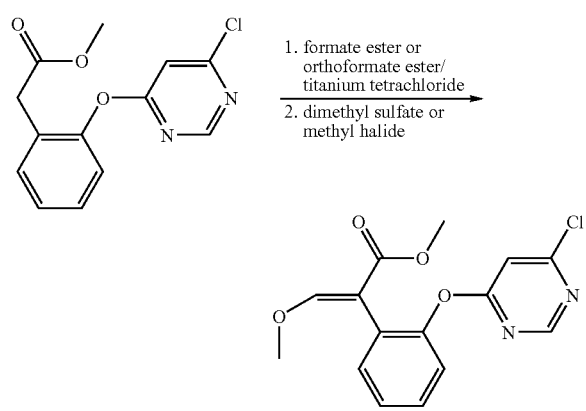

Under the dried nitrogen atmosphere, to a reaction flask were added 150 mL of dichloromethane and 11.4 g of titanium tetrachloride, and then 6.4 g of trimethyl orthoformate was further added under violent stirring. After being stirred at room temperature for 1 hr, the mixture was cooled to −5° C., followed by adding thereto 13.9 g of methyl 2-(2-(6-chloropyrimidin-4-oxy)phenyl)acetate. The resultant was stirred for 30 min, and then 12.1 g of triethylamine was added and the resultant was stirred for 1 hr. The resulting reaction mixture was washed with 40 mL of 10% hydrochloric acid, dried with anhydrous magnesium sulfate and evaporated under vacuum to obtain a brown viscous substance. The brown viscous substance was dissolved in 100 mL of hot toluene, cooled to room temperature and then treated with 0.9 g of benzyltriethylammonium chloride, 15 g of 20% sodium hydroxide aqueous solution and 12.6 g of dimethyl sulfate. After that, the mixture was stirred at room temperature for 5 hrs, followed by being heated to 50° C., and the reaction went on under stirring for another 1 hr. The resulting mixture was washed with 50 mL of water, evaporated under reduced pressure and purified with flash column chromatography to obtain 14.6 g pale yellow solid. The yield was 91%.

Melting point: 94-95° C.;
$^1$H NMR (500 NMR, CDCl$_3$): δ 3.60 (s, 3H), 3.73 (s, 3H), 6.78 (d, 1H), 7.17-7.42 (m, 4H), 7.45 (s, 1H), 8.58 (d, 1H).

EXAMPLE 4

Preparation of methyl (E)-2-(2-hydroxy)phenyl-3-methoxyacrylate

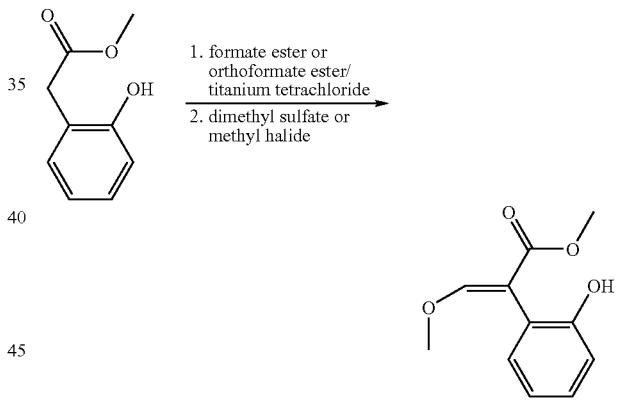

Under the dried nitrogen atmosphere, to a reaction flask were added 150 mL of dichloromethane and 11.4 g of titanium tetrachloride, and then 6.4 g of trimethyl orthoformate was further added under violent stirring. After being stirred at room temperature for 1 hr, the mixture was cooled to −5° C., followed by adding thereto 8.3 g of methyl 2-(2-hydroxy)phenyl acetate. The resultant was stirred for 30 min, and then 12.1 g of triethylamine was added and the resultant was stirred for 1 hr. The resulting reaction mixture was washed with 40 mL of 10% hydrochloric acid, dried with anhydrous magnesium sulfate and evaporated under vacuum to obtain a brown viscous substance. The brown viscous substance was dissolved in 100 mL of hot toluene, cooled to room temperature and then treated with 0.9 g of benzyltriethylammonium chloride, 15 g of 20% sodium hydroxide aqueous solution and 12.6 g of dimethyl sulfate. After that, the mixture was stirred at room temperature for 5 hrs, followed by being heated to 50° C., and the reaction went on under stirring for another 1 hr. The resulting mixture was washed with 50 mL of water, evaporated under reduced pressure and purified with flash column chromatography to obtain 9.2 g yellow solid. The yield was 88%.

Melting point: 125-126.5° C.;

$^1$H NMR (500 NMR, CDCl$_3$): δ 3.70 (s, 3H), 3.83 (s, 3H), 6.68 (d, 1s), 6.82-7.02 (m, 2H), 7.12-7.32 (m, 2H).

EXAMPLES 5 to 12

Preparation of methyl (E)-2-(2-(6-(2-cyanophenoxy) pyrimidine-4-oxy)phenyl)-3-methoxyacrylate (i.e. azoxystrobin) Under Different Reaction Conditions Azoxystrobin was prepared under different temperatures shown below according to the method of Example 2. The results are listed in table 1, wherein dichloromethane in examples 7 and 8 was replaced by dimethyl sulfoxide.

TABLE 1

Preparation of Azoxystrobin under Different Reaction Temperatures (R.T.)

| Example No. | R.T. in step (1) (° C.) | R.T. in step (2) (° C.) | Yield (%) |
|---|---|---|---|
| 5 | −10 to 10 | 20 to 50 | 90 |
| 6 | 0 to 25 | −10 to 30 | 80 |
| 7 | 50 to 80 | 80 to 100 | 25 |
| 8 | 150 to 180 | 50 to 80 | 10 |

Also, azoxystrobin was prepared under different reaction agents shown below according to the method of Example 2. The results are listed in table 2.

TABLE 2

Preparation of Azoxystrobin with Different Reaction Agents

| Example No. | Lewis acid | Formylating agent | Organic base | alkali | Methylating agent | Yield (%) |
|---|---|---|---|---|---|---|
| 9 | titanium tetrachloride | methyl formate | trimethyl amine | potassium carbonate | chloromethane | 74 |
| 10 | aluminium trichloride | trimethyl orthoformate | triethyl amine | potassium hydroxide | dimethyl sulfate | 35 |
| 11 | ferric chloride | Ethyl formate | triethyl amine | sodium hydroxide | iodomethane | 15 |
| 12 | titanium tetrachloride | trimethyl orthoformate | tributyl amine | sodium hydroxide | dimethyl sulfate | 88 |

EXAMPLE 13

Preparation of methyl (E)-2-(2-methoxy)phenyl-3-methoxyarylate

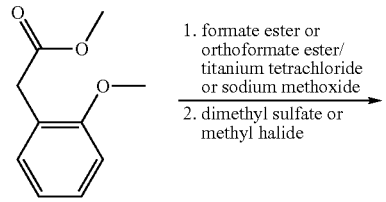

1. formate ester or orthoformate ester/ titanium tetrachloride or sodium methoxide
2. dimethyl sulfate or methyl halide

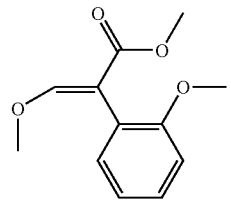

Under the dried nitrogen atmosphere, to a reaction flask were added 110 mL of dichloromethane and 8.6 g of titanium tetrachloride, and then 4.8 g of trimethyl orthoformate was further added under violent stirring. After being stirred at room temperature for 1 hr, the mixture was cooled to −5° C., followed by adding thereto 6.83 g of methyl 2-(2-methoxy) phenyl acetate. The resultant was stirred for 30 min, and then 9.1 g of triethylamine was added and the resultant was stirred for 1 hr. The resulting reaction mixture was washed with 30 mL of 10% hydrochloric acid, dried with anhydrous magnesium sulfate and evaporated under vacuum to obtain a brown viscous substance. The brown viscous substance was dissolved in 100 mL of hot toluene, cooled to room temperature and then treated with 0.7 g of benzyltriethylammonium chloride, 11 g of 20% sodium hydroxide aqueous solution and 9.5 g of dimethyl sulfate. After that, the mixture was stirred at room temperature for 5 hrs, followed by being heated to 50° C., and the reaction went on under stirring for another 1 hr. The resulting mixture was washed with 50 mL of water, evaporated under reduced pressure and purified with flash column chromatography to obtain 7.7 g oily substance. The yield was 92%.

Melting point: 125-126.5° C.;

$^1$H NMR (500 NMR, CDCl$_3$): δ 3.69 (s, 3H), 3.78 (s, 3H), 3.85 (s, 3H), 6.80-7.01 (m, 2H), 7.13-7.33 (m, 2H), 7.43 (s, 1s).

Industrial Practicability

The novel method for preparing a compound of general formula (I) according to the present invention has a simplified process and a high productivity. The reaction agents, vessels and various instruments used in the present invention are easily accessible or can be purchased from suppliers. The whole method needs no special reaction condition, has simple procedures and is easy to be industrialized.

What is claimed is:

1. A method for preparing a compound of general formula (I),

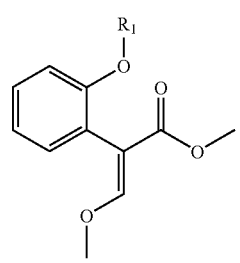

wherein $R_1$ is 6-(2-cyanophenoxypyrimidin)-4-yl or pyrimidin-4-yl substituted by a halogen atom at site 6, the method comprising the steps of:

(1) reacting a compound of general formula (II) with a formylating agent in an aprotic solvent in the presence of a Lewis acid at a temperature ranging from −20° C. to 200° C., and adding an organic base to promote the reaction so that an intermediate product is obtained,

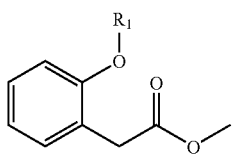

(II)

wherein $R_1$ has the same definition as $R_1$ in general formula (I);

(2) isolating the intermediate product produced by step 1;
(3) reacting the isolated intermediate product obtained in step (2) with a methylating agent in the presence of an alkali at a temperature ranging from −20° C. to 100° C. to obtain the compound of general formula (I).

2. A method according to claim 1, wherein the Lewis acid is selected from the group consisting of titanium tetrachloride, aluminum trichloride, methylaluminum chloride, tin chloride, ferric chloride, zinc chloride, boron trifluoride ethyl ether and combinations thereof.

3. A method according to claim 1, wherein the organic base includes amine and metal alkoxide.

4. A method according to claim 3, wherein the organic base is a tertiary amine.

5. A method according to claim 1, wherein the formylating agent includes methyl formate, ethyl formate, trimethyl orthoformate, triethyl orthoformate, and combinations thereof.

6. A method according to claim 1, wherein the alkali is comprised of sodium hydroxide, potassium hydroxide, sodium carbonate, potassium carbonate, sodium bicarbonate, potassium bicarbonate, sodium methoxide, sodium ethoxide, sodium tertiary butoxide and combinations thereof.

7. A method according to claim 1, wherein the methylating agent is comprised of dimethyl sulfate, trimethyl orthoformate, chloromethane, bromomethane, iodomethane and combinations thereof.

8. A method according to claim 1, wherein the step (1) is conducted at a temperature ranging from −20° C. to 100° C.

9. A method according to claim 1, wherein the aprotic solvent is comprised of a halogenated hydrocarbon, benzene, saturated hydrocarbon, dimethyl sulfoxide and combination thereof.

10. A method according to claim 1, wherein the methylation reaction in step (3) is conducted in a solvent selected from the group consisting of benzene, toluene, chlorobenzene, dichloromethane, dichloroethane, methanol, ethanol, butanol, ethyl ether, 1,2-dimethoxyethane, tetrahydrofuran, acetone, methyl ethyl ketone, methyl isobutyl ketone, ethyl acetate, isopropyl acetate, propyl acetate, butyl acetate and combinations thereof.

11. The method of claim 4 wherein the tertiary amine is selected from the group of trimethyl amine, triethyl amine, tributyl amine, diisopropylethyl amine and combinations thereof.

12. The method of claim 8 wherein the temperature of step (1) is between −10° C. and 50° C.

13. The method of claim 12 wherein the temperature of step (1) is between −5° C. and 5° C.

14. The method of claim 1 wherein the temperature of step (3) is between −10° C. and 80° C.

15. The method of claim 14 wherein the temperature of step (3) is between 10° C. and 60° C.

* * * * *